(12) United States Patent
Borycka et al.

(10) Patent No.: US 11,517,250 B2
(45) Date of Patent: Dec. 6, 2022

(54) METHOD TO ASSESS PELVIC FLOOR MUSCLES INJURY, AND PROBE AND APPARATUS TO IMPLEMENT THE METHOD

(71) Applicant: OASIS Diagnostics SA, Konstantynow Lodzki (PL)

(72) Inventors: Katarzyna Borycka, Warsaw (PL); Tadeusz Palko, Warsaw (PL); Wlodzimierz Lukasik, Mokre (PL)

(73) Assignee: OASIS Diagnostics SA, Konstanlynow Lodzki (PL)

( * ) Notice: Subject to any disclaimer, the term of this patent is extended or adjusted under 35 U.S.C. 154(b) by 946 days.

(21) Appl. No.: 15/577,240

(22) PCT Filed: May 27, 2016

(86) PCT No.: PCT/PL2016/050024
§ 371 (c)(1),
(2) Date: Nov. 27, 2017

(87) PCT Pub. No.: WO2016/190763
PCT Pub. Date: Dec. 1, 2016

(65) Prior Publication Data
US 2018/0153462 A1    Jun. 7, 2018

(30) Foreign Application Priority Data

May 27, 2015    (PL) .......................... 412485

(51) Int. Cl.
*A61B 5/00* (2006.01)
*A61B 5/0538* (2021.01)
(Continued)

(52) U.S. Cl.
CPC .......... *A61B 5/4255* (2013.01); *A61B 5/0538* (2013.01); *A61B 5/287* (2021.01);
(Continued)

(58) Field of Classification Search
CPC . A61B 5/0422; A61B 5/04884; A61B 5/6873; A61B 5/227; A61B 5/287;
(Continued)

(56) References Cited

U.S. PATENT DOCUMENTS 5,562,717 A * 10/1996 Tippey .................. A61B 5/227
607/138
6,741,895 B1 * 5/2004 Gafni ................... A61B 5/4337
600/38
(Continued)

FOREIGN PATENT DOCUMENTS

WO      99/35968      7/1999
WO      00/23030      4/2000

*Primary Examiner* — Eun Hwa Kim
(74) *Attorney, Agent, or Firm* — ALGM LLP; Harry J. Guttman

(57) ABSTRACT

The object of the present invention is the method to assess the pelvic floor muscle injury, comprising the steps of applying the measuring probe into the anus, generation of electric current signals of constant amplitude, using a current generator, and applying the signals into the pelvic floor muscles by means of application electrodes (EA1) and (EA2), detection of electric voltage signals from the pelvic floor muscles by means of a plurality of measuring electrodes (EP1), EP2 . . . EPn, analysis of electric current and voltage signals for amplitude values and phase dependencies of their waveform, wherein the electric current signals and the electric voltage signals from the pelvic bottom muscles constitute signals variable in time, of the frequencies ranging from 2 kHz to 200 kHz. The object of the invention is also an electrode based measuring probe and apparatus implementing the method of assessment pelvic floor muscles injury.

8 Claims, 6 Drawing Sheets

Figure 1:
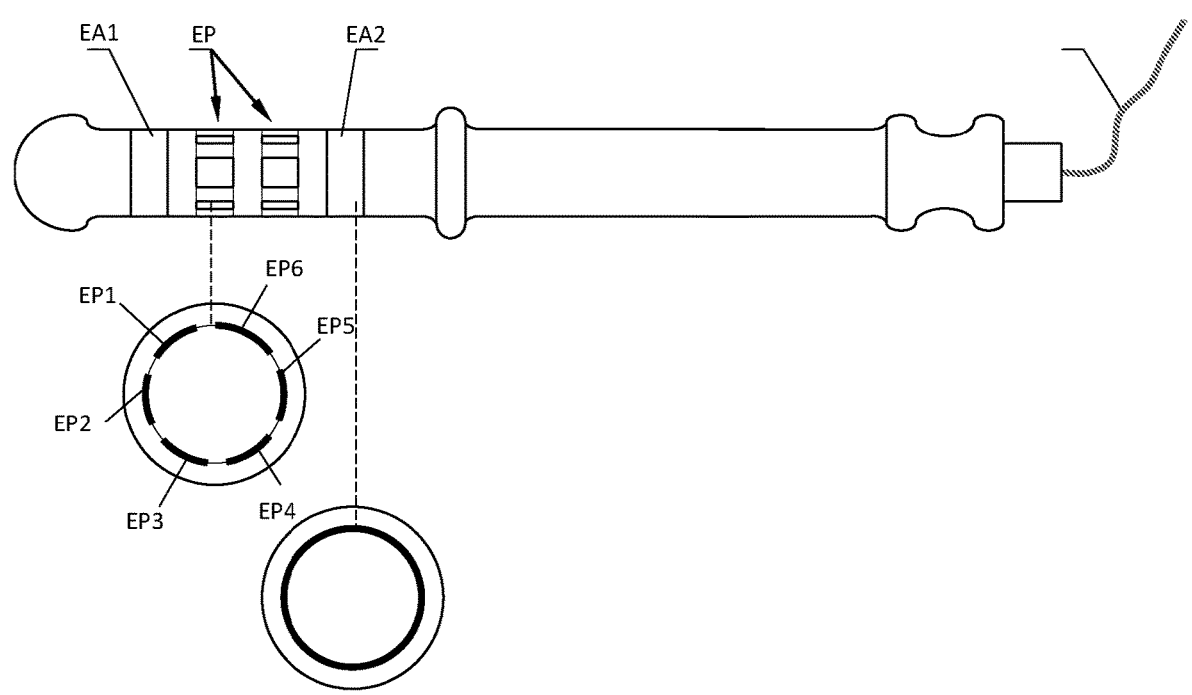

(51) Int. Cl.
  *A61B 5/287* (2021.01)
  *A61B 5/392* (2021.01)
  *A61N 1/05* (2006.01)
  *A61B 5/391* (2021.01)

(52) U.S. Cl.
  CPC ............ *A61B 5/392* (2021.01); *A61B 5/4519* (2013.01); *A61B 5/6873* (2013.01); *A61B 5/391* (2021.01); *A61B 2562/0209* (2013.01); *A61B 2562/043* (2013.01); *A61N 1/0512* (2013.01)

(58) Field of Classification Search
  CPC ....... A61B 5/4519; A61B 5/389; A61B 5/224; A61B 5/24; A61B 5/388; A61B 5/391; A61B 2562/0209; A61B 17/8066; A61N 1/0512; A61N 1/36007; A61N 1/0514
  See application file for complete search history.

(56) References Cited

U.S. PATENT DOCUMENTS

| | | | |
|---|---|---|---|
| 9,199,078 B1 * | 12/2015 | Gunderson | A61N 1/3925 |
| 2002/0173784 A1 * | 11/2002 | Sliwa, Jr. | A61B 17/22012 |
| | | | 606/28 |
| 2005/0113877 A1 * | 5/2005 | Spinelli | A61N 1/36107 |
| | | | 607/39 |
| 2007/0100387 A1 * | 5/2007 | Gerber | A61B 5/204 |
| | | | 607/41 |
| 2011/0118805 A1 * | 5/2011 | Wei | A61N 1/36007 |
| | | | 607/41 |
| 2012/0101545 A1 * | 4/2012 | Wahlstrand | A61N 1/37288 |
| | | | 607/60 |
| 2012/0265044 A1 * | 10/2012 | Broens | A61B 5/42 |
| | | | 600/373 |

* cited by examiner

METHOD TO ASSESS PELVIC FLOOR MUSCLES INJURY, AND PROBE AND APPARATUS TO IMPLEMENT THE METHOD

The object of the invention is the method to assess the damage to the pelvic floor muscles and a probe and apparatus to implement the method applicable in pelvic floor muscles diagnostics, in particular in impairment of the anal sphincter system and flatal and/or fecal incontinence resulting from vaginal delivery.

Flatal and/or fecal incontinence is a set of clinical symptoms resulting from inefficiency of the sphincter mechanisms closing the anus. Loss of control on defecation, lack of possibility to differentiate between flatulence and feces and uncontrolled gas escape negatively influence the quality of life, are the cause for the disability eliminating the patient from social life and significantly reducing their activity in the family. Fecal incontinence requires careful diagnostics and its treatment is difficult. There are only a few reference centers in Europe dealing with the problems of fecal incontinence (e.g. in Holland, Germany, Austria, and Italy). The diagnostic-therapeutic procedure algorithms, such as those presented in the following scientific publications: Whiteed W. E. et al., "Treatment options of fecal incontinence," Dis. Colon. Rectum. 2001, 44, 131-144; Herman R. et al., "Modern diagnostics and treatment option of fecal incontinence," Postępy Nauk Medycznych [*Medical Science Progress*], 2006, 5, 216-234; Campbell B., "Recent NICE guidance of interest to surgeons," Ann. R. Coll. Surg. Engl. 2014 July, 96(5), 402-3; Vitton V. et al., "Treatments of faecal incontinence: recommendations from the French national society of coloproctology," Colorectal Dis., 2014 March, 16(3), 159-66, that have been functioning for a dozen of years only, are still subject to modifications, and audits assessing their implementation in practice indicate significant deficits both in the scope of diagnostics and in treatment of fecal incontinence (Harari D. et al. "National audit of continence care: adherence to National Institute for Health and Clinical Excellence (NICE) guidance in older versus younger adults with faecal incontinence," Age Ageing, 2014 November, 43(6), 785-93).

The most common cause for anal sphincter injury, leading in consequence to fecal incontinence, is obstetric pelvic floor muscles injury in vaginal delivery course. The symptoms of incontinence after spontaneous vaginal delivery are observed at 13-25% patients (Nordeval et al., "Anal incontinence after obstetric sphincter tears: outcome of anatomic primary repairs," Dis Colon Rectum, 2005, 48, 1055; Abramowitz L. et al., "Are sphincter defects the cause of anal incontinence after vaginal delivery? Results of a prospective study," Dis Colon Rectum, 2000, 43, 590-596; McArthur C. et al., "Obstetric practice and faecal incontinence 3 months after delivery," Br J Obstet Gynecol, 2001, 108, 6798-683; Hannah M. E. et al., "Outcomes at 3 months after planned cesarean vs planned vaginal delivery for breech preservation at term: the international randomized Term Breech Trail," JAMA, 2002, 287, 1822-1831; Hall et al., "Frequency and predictors for postpartum fecal incontinence," Am J Obstet Gynecol, 2003, 188, 1205-1207), including 13% primiparas and 23% multiparas. Whereas in ultrasonic imaging (EUS) the features of anal sphincter injury are found in almost 40% of birth-giving women (Sudoł-Szopińska I. at al., "Diagnostyka poporodowych uszkodzeń mięśni dna miednicy," [*Diagnostics of obstetric defects of the pelvic floor*], Ginekologia Praktyczna [*Practical Gynaecology*], 2007, 1, 22-31), which indicates that in a certain group of patients, the features of anatomic sphincter injury are present despite the lack of clinically visible symptoms of fecal incontinence. They can manifest and intensify even many years later when other factors weakening the muscles add in (age, menopause, undergone surgeries).

The frequency of obstetric anal sphincter injuries is higher than it has been thought, and such factors as: extended II phase of labor, uncontrolled perineal tear, or forceps delivery bring about even higher risk of incontinence symptoms occurrence (Evans C. et al., "Management of obstetric anal sphincter injuries (OASIS) in subsequent pregnancy," J Obstet Gynaecol., 2014 August, 34(6), 486-8). However, even proper delivery can be the cause for fecal incontinence. Postpartum dysfunction of the sphincter system can result from direct damage to the sphincter muscle tissue or its coexistence with the damage to the pudendal nerve. The most common type of obstetric injury is a partial external anal sphincter injury, usually undetectable during labor and delivery. The percentage of unrecognized obstetric anal sphincter injuries is as high as 35% (Kołodziejczak M. i et al., "Anal endosonographic findings in women after vaginal delivery," Eur J Radiol, 2011, 78, 157-159). In endosonographic examination, damage to either one or both anal sphincters is found at 35% of primiparas and 44% of multiparas. In case of multiparas, consecutive deliveries increase the risk of injury, and they can also cause the so far symptomless injuries to manifest clinically. It is believed that what is also significant is the age above 35 years, family history of incontinence and episiotomy whose performance more than doubles the incontinence risk in comparison with women with perineal protection (Espuña-Pons M. et al., "Double incontinence in a cohort of nulliparous pregnant women," Neurourol Urodyn., 2012, 31(8), 1236-41).

Obstetric anal sphincter injury can be obvious, when III or IV grade perineal tear occurs, and concealed, invisible and undiagnosed during labor and delivery. Diagnosed rupture of anal sphincter muscles requires urgent dressing, not later than within 24 hours. Originally undressed anal sphincter muscle rupture requires designation of protective stoma and reconstructive surgery in delayed mode, usually after 6 months. The results of reconstructive surgeries are still not satisfactory. Therefore, diagnosing the injury within 24 hour, which would allow for its single-stage and most effective dressing, is of key importance here Patients with obstetric flatal/fecal incontinence symptoms, both after the original dressing of torn muscles and those with neurogenic injury, require intensive specialist treatment. Necessary in those cases: deepened diagnostics (transrectal USG, anorectal manometry), and then rehabilitation treatment (EMG-biofeedback, functional stimulation), require knowledge and experience possessed by only a small group of experts dealing in detail with the pelvic floor dysfunctions.

In this aspect, it is of key importance to create a possibility to run quick and precise diagnostics of obstetric injuries that will help to separate, from among women after deliver, a group with injuries requiring immediate surgery dressing within 24 hours or expert (coloproctology) consultation as soon as possible, and rehabilitation or even surgical treatment in delayed mode. Diagnostics performed in such cases comprises transrectal USG (assessing the morphology of sphincters) and anorectal manometry (precisely assessing the function of the sphincters and lower rectum) performed usually ca. 12 weeks after delivery. The availability of those examinations is small, not only due to the high cost of diagnostic apparatus, but first of all due to high qualifications required from the experts interpreting their results.

The object of the invention presented in U.S. Pat. No. 5,875,778 is an electrode for stimulation and fro detection of patient's muscles activity, wherein the electrode is applied into the body cavity. The electrode is suitable for stimulation and/or detection of activity of muscles, such as female pelvic bottom muscles, and can be applied to treat ailments connected with the anal sphincter. The electrode has the shape of an elongated body placed in a body cavity, upon the surface of which electric contacts have been arranged, receiving bioelectric signals from appropriate muscles.

On the other hand, U.S. Pat. No. 6,185,465 discloses an electrode applied into a body cavity during treatment, e.g. urinal incontinence treatment. The electrode includes a rod-shaped body composed of non-conductive material with a plurality of ring-shaped conductive bands disposed apart from one another along a longitudinal axis of the main body, and a plurality of electrical lines connected to corresponding bands is buried within main body, extend through a rear side of the main body, and couples electrically to the controller. The electrode placed in a body cavity, e.g. patient's rectum or vagina, stimulates the examined muscles with appropriate electrical signals, on the one hand, and receives EMG signals originating from the stimulated muscles, on the other hand, allowing to determine the activity of the examined muscles with the bio-feedback method.

International patent application WO2005096926 discloses a sensor for myoelectric signal detection, comprising a cylindrical base, on which at least one electrode array is disposed that is composed of electrodes which are evenly distributed along the cylindrical base circumference, said electrodes being able to detect electric currents created by the action of muscle, particularly a sphincter. In one embodiment of the quoted invention, the sensor comprises two peripherally arranged electrode arrays forming rings, said rings being at a short distance from one another along the longitudinal axis of the cilinder, and each ring consists of twelve electrodes evenly distributed along the perimeter of the cylindrical base.

From European patent No. EP2029220, a medical probe is known for pelvic floor muscle electrostimulation and training for diagnostic and physiotherapeutic purposes. The said probe has a body which is insertable into a vagina or a rectum, and a plurality of electrodes which are appropriately positioned on the outer surface of said probe. The arrangement of a plurality of electrodes along the length and the perimeter of the body and connecting the probe with a control unit capable of receiving electromyographic signals from each electrode enable, after appropriate data processing with specialist computer software, three-dimensional mapping of the pelvic floor muscles reactions. The control unit, having received EMG response from pelvic floor muscles, assesses the parameters of the electric signal stimulating pelvic floor muscles in order to stimulate, and thus training the same.

The technical problem faced by the present invention is to provide such a method to assess the pelvic floor muscles, and a probe and apparatus to implement the same that will allow for fast and noninvasive detection of muscle injury in this area, that will allow for identification of the damaged place, with the possibility to describe the same by means of simple physical quantities and will provide repeatable, exact and easy to interpret result of such assessment, of simple structure and inexpensive in production, and the assessment itself easy to conduct. Unexpectedly, the said technical problems have been solved in the present invention.

The first object of the present invention is the method to assess the pelvic floor muscle injury, comprising the following steps:
a) application of the probe into the rectum,
b) generation, using a generator, of electric signals of constant amplitude and applying them into the pelvic floor muscles by means of application electrodes EA1 and EA2,
c) detection of electric voltage signals from pelvic floor muscles, being response to the electric current from electrodes EA1 and EA2 by a plurality of measurement electrodes EP1, EP2 . . . EPn,
d) analysis of electric current and voltage signals for amplitude values and phase dependencies of their waveform, characterized in that the electric current signals and the electric voltage signals from the pelvic bottom muscles constitute signals variable in time, of the frequencies ranging from 2 kHz to 200 kHz.

In a preferred embodiment of the present invention the electric current signals and the electric voltage signals from the pelvic bottom muscles constitute signals variable in time, of the frequencies ranging from 2 kHz to 50 kHz.

In a preferred embodiment of the present invention, the electric current signals in step b) have a constant amplitude, not causing tissue depolarization, preferably below 1 mA.

In another preferred embodiment of the present invention, the electric voltage signals from the pelvic floor muscles constitute the electric impedance measure.

In another preferred embodiment of the present invention, in step d) the phase shift angle and the electric impedance module are analyzed.

The second object of the present invention is an electrode based measuring probe for assessment of pelvic floor muscles injury, comprising a cylindrical main body with two application electrodes EA1 and EA2 and a plurality of measurement electrodes EP1, EP2 . . . EPn, arranged on its surface, each electrode having an electrical contact extending in the rear part of the cylindrical body, characterized in that the application electrode EA1 is the furthest disposed electrode towards the front end of the measuring electrode probe, and the application electrode EA2 is the closest disposed electrode towards the front end of the measuring electrode probe, whereas a plurality of measurement electrodes EP1, EP2 . . . EPn are disposed between the application electrodes EA1 and EA2.

In a preferred embodiment of the present invention, a plurality of measurement electrodes EP1, EP2 . . . EPn assume the form of ring sections, preferably arranged in two ring structures.

The third object of the present invention is the apparatus to assess the pelvic floor muscle injury, characterized in that it comprises the electrode based measuring probe as defined in the second object of the present invention, and an impedance spectrometer to measure electric activity of tissues, the apparatus implementing the method described in the first object of the present invention.

The method to assess pelvic floor muscle injury using electric impedance measurement, in particular phase shift angle and the impedance module, enables for fast, repeatable and non-invasive assessment of pelvic floor muscles and detection of its damage, particularly the clinically hidden ones. The probe according to the innovation, due to its specific shape and having the electrodes disposed upon its surface, and independent analysis of the signal from each electrode, enables not only detection of damage to the muscle, but also its localization, and allows to determine its mechanism (muscle tear or stretching) easily. Furthermore, it is possible to make the assessment even directly after injury, without the risk of additional damage, and the probe itself can be precisely applied in the examined area.

Figure 2:
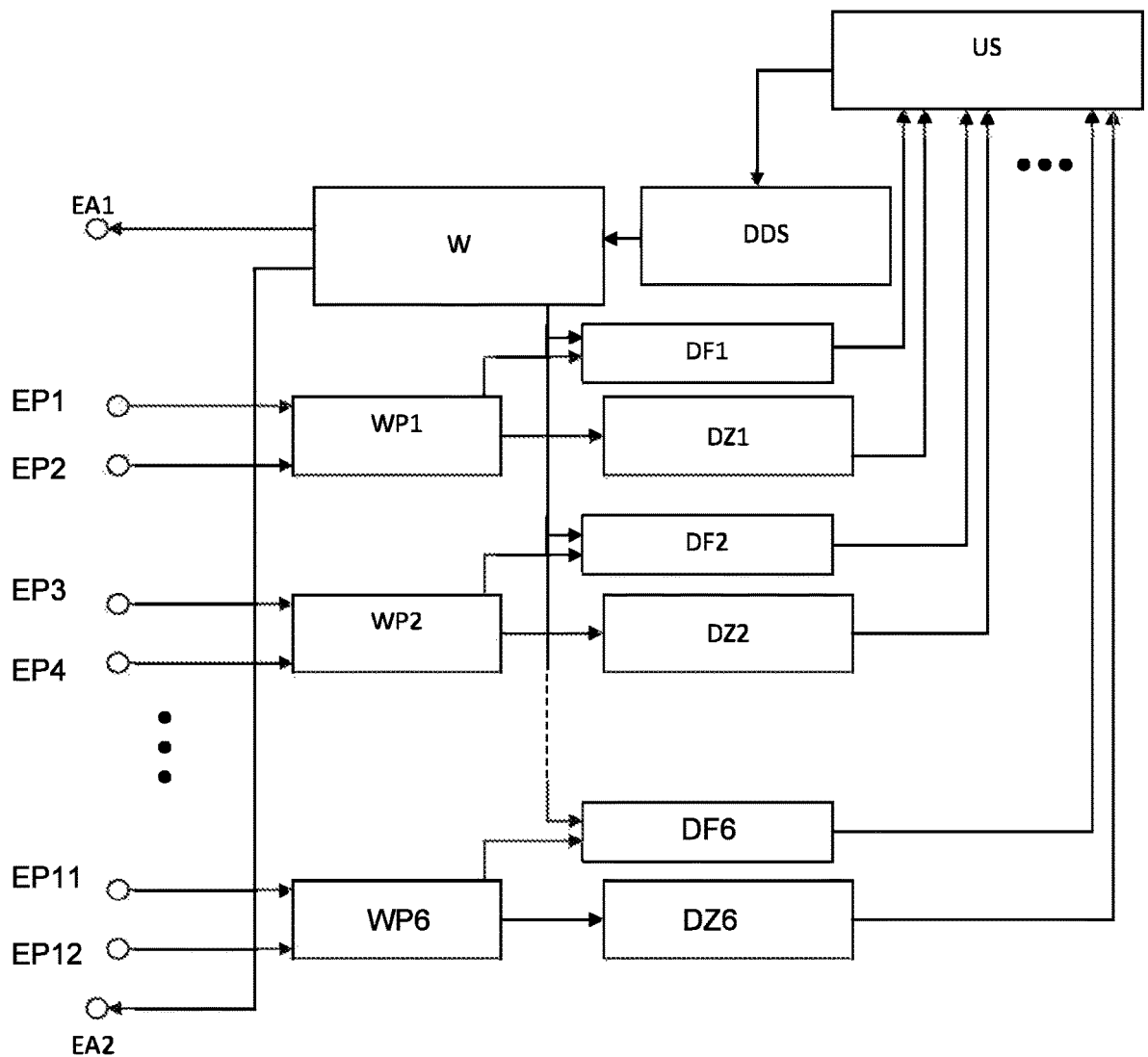
Figure 3:
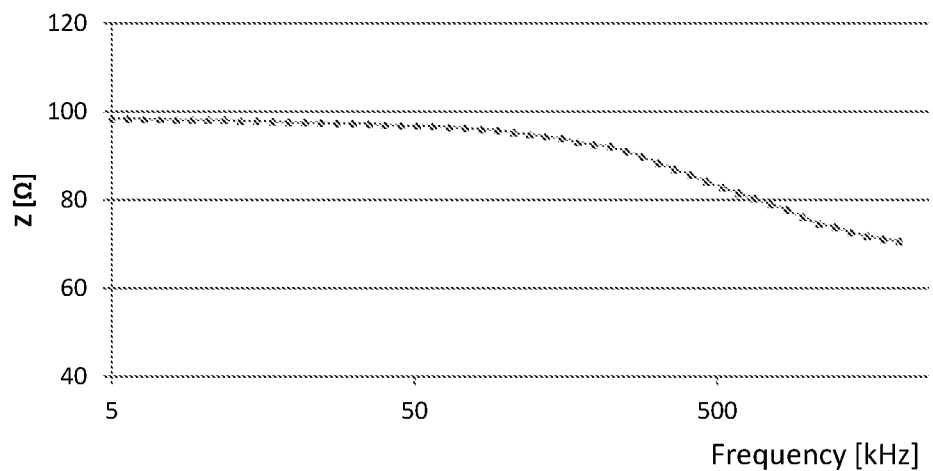
Figure 3:
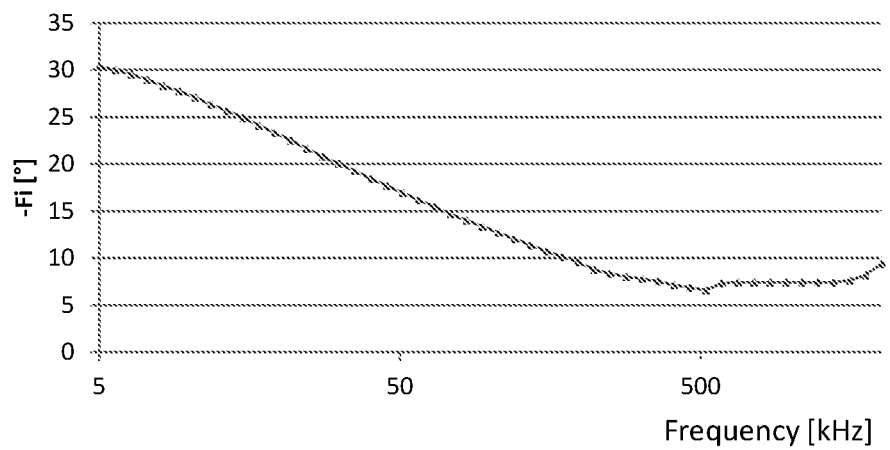
Figure 4:
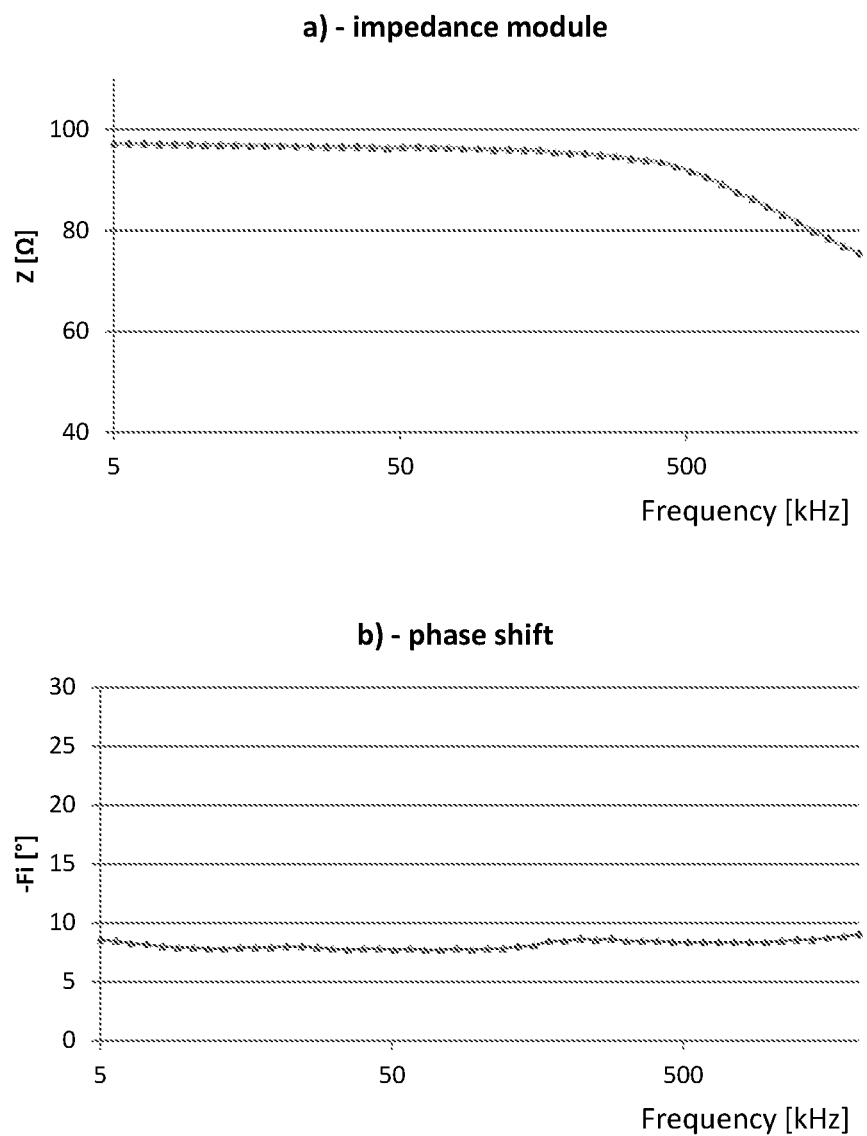
Figure 5:
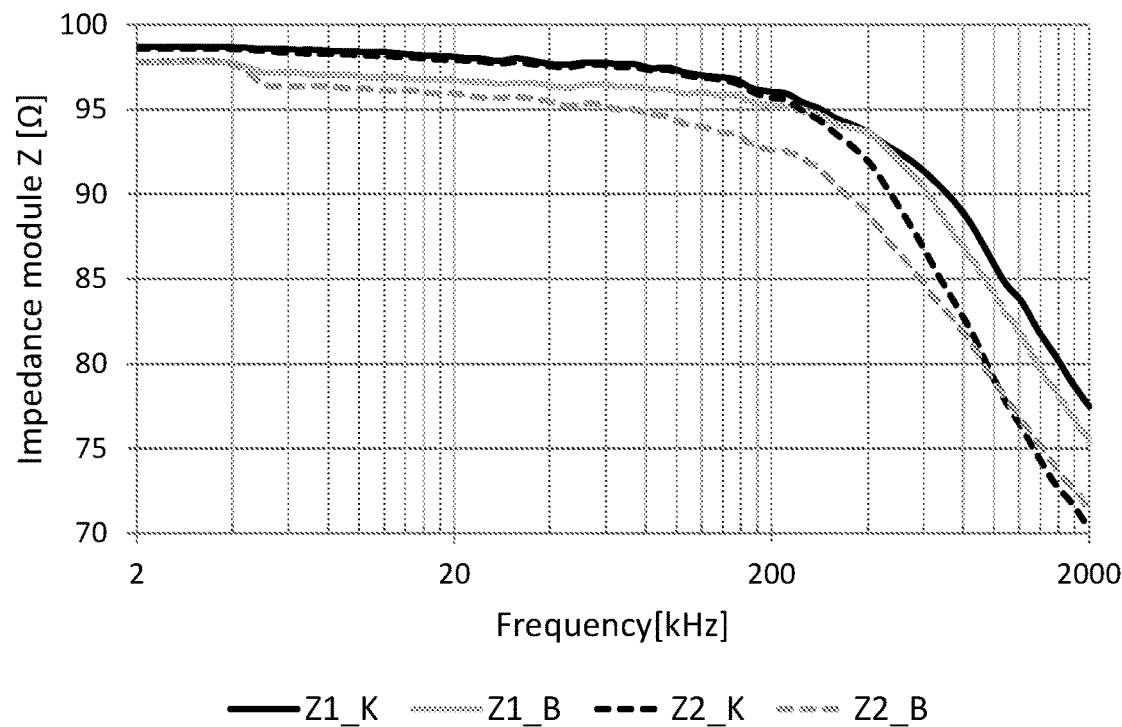
Figure 6:
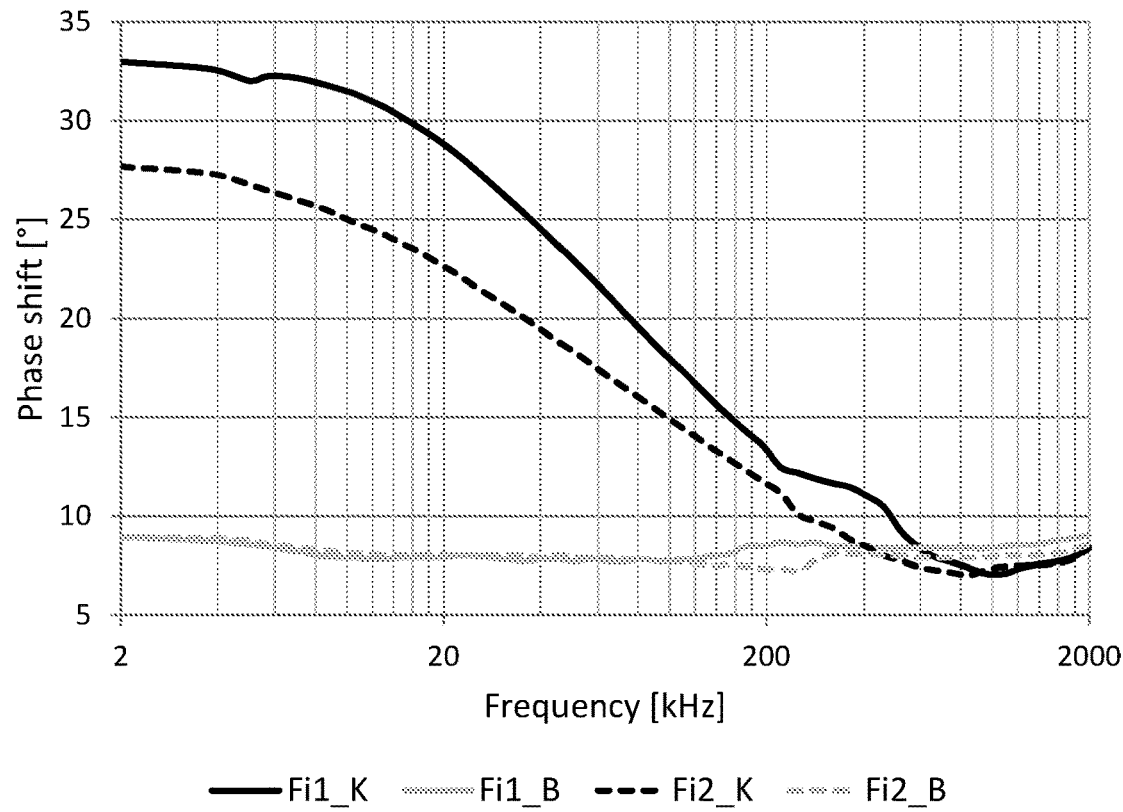
Figure 7:
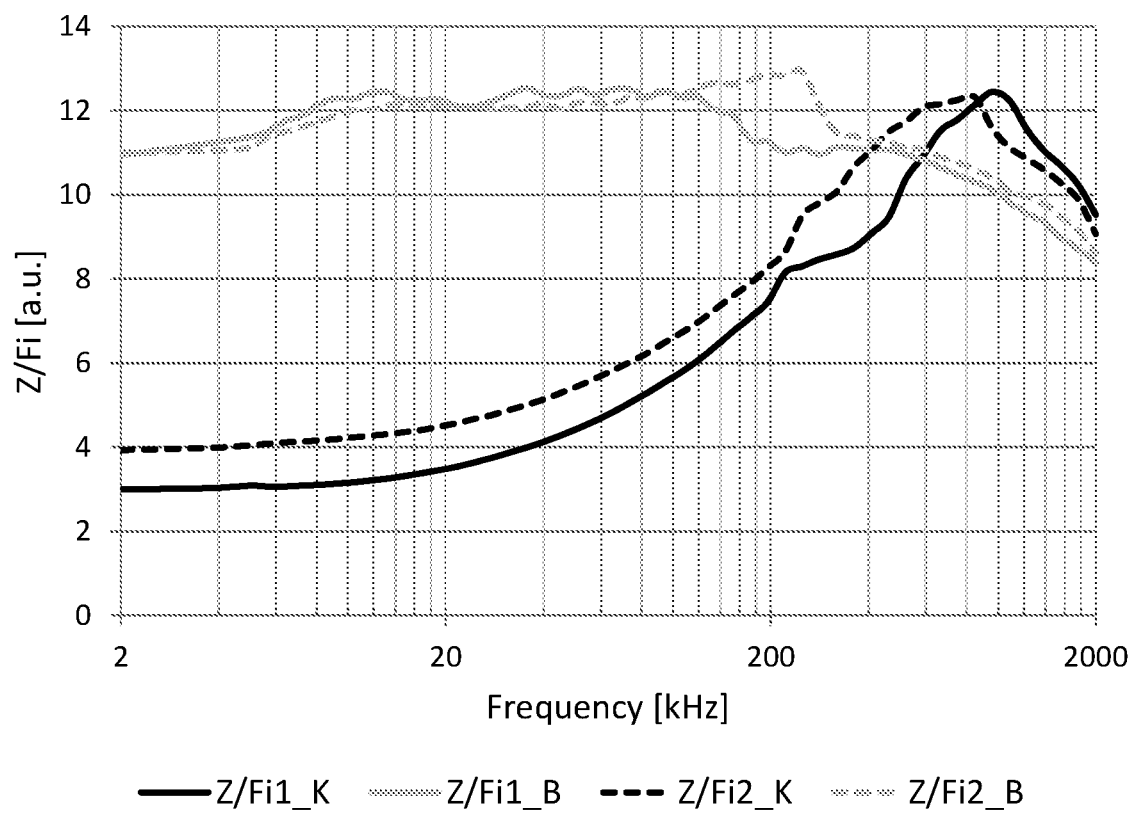

Exemplary embodiments of the invention have been presented in the drawings, wherein FIG. 1 presents a lateral view of the electrode based measuring probe, accompanied with two schematic cross-sections, FIG. 2 presents the block diagram of the apparatus for assessment of the pelvic floor muscle injury, FIG. 3 illustrates the results of impedance characteristics measurements in frequency function for a healthy patient, FIG. 4 illustrates the results of impedance characteristics measurements in frequency function for a patient with sphincter injury, FIG. 5 illustrates the collective chart for impedance module measurements in frequency function, FIG. 6 illustrates the collective chart for phase shift measurements in frequency function, whereas FIG. 7 illustrates the collective chart for the determined Z/Fi parameter in frequency function.

EXAMPLE 1

Having positioned the patient in half-seating position with lower limbs bent, having applied USG/EKG gel, the electrode based measuring probe, illustrated in FIG. 1, was applied into the patient's rectum, with the application electrodes EA1 and EA2 and measuring electrodes EP1-EP12 disposed along the section of 30 cm between locking elements (allowing its precise seating). Then, electrical stimulating signal was provided in the form of sinusoidal alternating current of the frequencies ranging from 1 kHz to 1 MHz. Next, the phase shift angle and the impedance module measurement was preformed, obtaining impedance spectrum. Further on, the response spectrum analysis was performed to identify characteristic features for regular and injured (by various mechanisms) pelvic floor muscles. An identical procedure was repeated for 12 patients with healthy pelvic floor muscles, and for 12 patients with already existing injury confirmed in standard diagnostic examination (transrectal USG and anorectal manometry). The experiment was carried out following a consent from Bioethics Committee (at the Regional Medical Chamber in Warsaw, No. KB/977/15). The example of obtained frequency waveforms of the impedance module (a) and the phase shift angle (b) for a healthy patient is presented in FIG. 3. The example of obtained frequency waveforms of the impedance module (a) and the phase shift angle (b) for a patient with diagnosed sphincter injury is presented in FIG. 4. The chart presented in FIG. 4 shows significant difference in the analysis of phase shift angle and the impedance module in 5-100 kHz frequency range, which is correlated with the damage to the sphincter muscles. The obtained differences in the examined parameters were analogical for all examined patients with diagnosed pelvic floor muscles injury, which confirms the repeatability of the assessment method used.

EXAMPLE 2

FIG. 1 represents a lateral view of the electrode based measuring probe according to the present invention, thanks to which the method to assess pelvic floor muscle injury according to the present invention is implemented. The probe consists substantially of a cylindrical body upon which two application electrodes EA1 and EA2 are disposes in such a way that the application electrode EA1 is the furthest disposed electrode towards the front end of the measuring electrode probe, and the application electrode EA2 is the closest disposed electrode towards the front end of the measuring electrode probe. Between the application electrodes EA1 and EA2, twelve measuring electrodes EP1-EP12 have been disposed in the form of continuous rings (which is shown in the schematic cross-section in the area of application electrode EA2). The measuring electrodes EP1-EP12 assumed the form of ring sections, disposed at an equal distance from one another, in the arrangement of six ring sections disposed in two rows of ring structures (which is shown in the schematic cross-section in the measuring electrodes EP1-EP6 area). The electrode based measuring probe has a locking element allowing for its precise seating. Electric wires PE, running inside the cylindrical body and extending outside the electrode based measuring probe are connected to all measuring and application electrodes, and are further connected to the impedance spectroscope.

The shape and the distribution of electrodes upon the electrode based measuring probe surface, and independent signal analysis from each electrode, not only enable detection of muscle injury, but also its localization, and they allow to determine its mechanism (muscle tear or stretching) easily. Furthermore, due to the construction of the electrode based measuring probe, it is possible to make the assessment even directly after injury, without the risk of additional damage, and the probe itself can be precisely applied in the examined area.

EXAMPLE 3

The apparatus for assessment of pelvic floor muscles injury comprises an electrode based measuring probe as defined in Example 2, and an impedance spectrometer to measure electric impedance of tissues.

FIG. 2 presents the block diagram of the impedance spectrometer system for assessment of the pelvic floor muscle injury. The presented system for assessment of pelvic floor muscle injury comprises: a control system US connected with electric signal generator DDS, which is in turn connected with the application current amplifier and adjustment system W electrically coupled with application electrodes EA1 and EA2. Twelve measuring electrodes EP1-EP12, coupled in pairs with corresponding measuring amplifiers WP1-WP6 (WP1, WP2, and WP6 are shown in the figure and WP3-WP5 are not shown), from which electrical signals arrive at corresponding impedance module detectors DZ1-DZ6 (DZ1, DZ2, and DZ6 are shown in the figure and DZ3-DZ5 are not shown) and phase detectors DF1-DF6 (DF1, DF2, and DF6 are shown in the figure and DF3-DF5 are not shown). Phase detectors DF1-DF6 compare the phase of electrical response signals with the phase of electric stimulating signals from the amplifier and application current control system W, and impedance detector modules DZ1-DZ6 and phase detectors DF1-DF6 are coupled with the control system US in order to transmit the measurement signals.

EXAMPLE 4

Upon obtaining positive opinion from Bioethics Committee, examinations were carried out on 5 female patients, healthy and with pelvic floor muscle injury symptoms with various risk factors (undergone deliveries, undergone proctologic surgeries). The examination was carried out using the electrode based measuring probe according to one embodiment of the present invention and a system comprising such electrode. In this embodiment, an electrode based measuring probe structurally convergent with the electrode probe presented in Example 2 was used, with that exception that instead of twelve measuring electrodes, four measuring electrodes EP1-EP4 were used. The measuring electrodes EP1-EP4 assumed the form of ring sections, disposed at an equal distance from one another, in an arrangement of four ring sections disposed in one row of ring structures. The course of examination was substantially convergent with the examination described in Example 1. Having performed medical examination, it was found that the impedance records from perirectal tissues differ significantly between healthy patients and patients with pelvic floor muscles injury (confirmed by USG and anorectal manometry). In the examination carried out with the two-spot method, the impedance module from group K (control, no pelvic floor muscles injury, n=3) and for patients from group B (with obstetric sphincter tear, n=2) looked like in the chart presented in FIG. 5. As can be seen from the chart referred to, the impedance module measurement is substantially convergent in the 2-200 kHz frequency range for healthy patients (Z1 K and Z2 K, Z1 K representing the impedance module measurement from two measuring electrodes EP1 and EP3 disposed opposite each other, whereas Z2 K represents the impedance module measurement from two measuring electrodes EP2 and EP4 disposed opposite each other, in the direction perpendicular to the EP1 and EP3 electrodes arrangement). The decrease of impedance module is observed within the same frequency range (Z1 B and Z2 B, Z1 B and Z2 B analogically representing impedance module measurement from measuring electrodes, EP1 and EP3, and EP2 and EP4, respectively) for female patients with diagnosed pelvic bottom muscles injury, which confirms effective operation of this invention.

Concurrently with the impedance module, the measurement of phase shift angle was carried out. FIG. 6 presents a chart for the measured phase shift angle in the function of frequency for healthy patients (Fi1 K and Fi2 K) and for patients with diagnosed pelvic floor muscles injury (Fi1 B and Fi2 B). Symbols on the chart curves correspond with the systematics used on measuring the impedance module. It can be noted once more that the visible differences in the phase shift angle, differentiating the examined patients for the presence of pelvic floor muscle injury, fall within the frequency range from 2 kHz to 2 MHz. In that range the differences are the most significant and allow to assess the occurrence of those injuries with the highest probability. Additionally, in FIG. 7, the dependence between the impedance module and the phase shift angle has been charted and marked as Z/Fi. The chart illustrates the difference in results between patients with healthy pelvic floor muscles (group K—Z/Fi1 K and Z/Fi2 K) and the patients with diagnosed pelvic floor muscle injury (group B—Z/Fi1_B and Z/Fi2_B). It can be seen on the presented chart that the Z/Fi coefficient separates pathological conditions from regular conditions very well within the frequency range of 2 to 200 kHz in the measured module Z value and phase angle Fi (impedance) value. Still more preferable range for differentiating pathological conditions is included within 2 to 50 kHz area. Within this frequency range the differences are the most conspicuous, which allows to determine the presence of pelvic floor muscles injuries with higher precision.

The invention claimed is:

1. A method to assess a pelvic floor muscles injury, comprising the following steps:
    a) application of a probe into a patient's rectum, wherein the probe comprises application electrodes (EA1) and (EA2), and a plurality of measuring electrodes (EP1), (EP2) . . . (EPn), wherein the plurality of measurement electrodes form one or more ring structure(s) that do not comprise an application electrode,
    b) generation, using a generator, of electric signals of constant amplitude and applying them into the pelvic floor muscles by means of application electrodes (EA1) and (EA2), without causing tissue depolarization,
    c) detection of electric voltage signals from the pelvic floor muscles by means of a plurality of measuring electrodes (EP1), (EP2) . . . (EPn),
    d) analysis of electric current and voltage signals for amplitude values and phase dependencies of their waveform,
    characterized in that the electric current signal and the electric voltage signals from the pelvic floor muscles constitute signals variable in time, of frequencies ranging from 2 kHz to 200 kHz, and
    characterized in that the electric voltage signals from the pelvic floor muscles correspond to an electric impedance measurement.

2. The method of claim 1, characterized in that the electric current signal and the electric voltage signals from the pelvic floor muscles constitute signals variable in time, of frequencies ranging from 2 kHz to 50 kHz.

3. The method of claim 1, characterized in that the electric current signals in step b) have a constant amplitude below 1 mA.

4. The method of claim 1, characterized in that in step d) a phase shift angle and an electric impedance module are analyzed.

5. An electrode based measuring probe for assessment of pelvic floor muscles injury, comprising a cylindrical main body, with two application electrodes (EA1) and (EA2) and a plurality of measurement electrodes ((EP1), (EP2) . . . (EPn)), arranged on its surface, each application electrode having an electrical contact extending in the rear part of the cylindrical body, characterized in that the application electrode (EA1) is the furthest disposed electrode towards the front end of the measuring electrode probe, and the application electrode (EA2) is the closest disposed electrode towards the front end of the measuring electrode probe, and further characterized in that the plurality of measurement electrodes are disposed between the application electrodes (EA1) and (EA2) and the plurality of measurement electrodes form one or more ring structure(s) that do not comprise an application electrode, wherein the electrode based measuring probe is configured to deliver electric application current having a constant amplitude that does not cause tissue depolarization and electric voltage signals from the pelvic floor muscles constitute an electric impedance measurement.

6. The electrode based measuring probe of claim 5, characterized in that the plurality of measurement electrodes assume the form of ring sections.

7. An apparatus for assessment of the pelvic floor muscles injury, characterized in that it comprises the electrode based measuring probe as defined in claim 6, and an impedance spectrometer to measure electric impedance of tissues.

8. The apparatus of claim 7, wherein the apparatus is capable of implementing a method to assess the pelvic floor muscles injury comprising the following steps:
    a) application of the probe into a patient's rectum,
    b) generation, using a generator, of electric signals of constant amplitude and applying them into the pelvic floor muscles by means of application of the electrodes (EA1) and (EA2), to apply the electric impedance measurement,
c) detection of electric voltage signals from the pelvic floor muscles by means of the plurality of measuring electrodes,
d) analysis of electric current and voltage signals for amplitude values and phase dependencies of their waveform, characterized in that the electric current signal and the electric voltage signals from the pelvic floor muscles constitute signals variable in time, of frequencies ranging from 2 kHz to 200 kHz.

* * * * *